(12) United States Patent
Takeda et al.

(10) Patent No.: US 8,809,509 B2
(45) Date of Patent: *Aug. 19, 2014

(54) PROTEIN PURIFICATION METHOD

(71) Applicant: Chugai Seiyaku Kabushiki Kaisha, Tokyo (JP)

(72) Inventors: Kozo Takeda, Tokyo (JP); Norimichi Ochi, Tokyo (JP); Kimie Ishii, Tokyo (JP); Manabu Matsuhashi, Tokyo (JP); Akinori Imamura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/847,691

(22) Filed: Mar. 20, 2013

(65) Prior Publication Data

US 2013/0225796 A1    Aug. 29, 2013

Related U.S. Application Data

(62) Division of application No. 10/527,455, filed as application No. PCT/JP03/11642 on Sep. 11, 2003, now Pat. No. 8,420,789.

(30) Foreign Application Priority Data

Sep. 11, 2002 (JP) ................................. 2002-265609

(51) Int. Cl.
*C07K 1/00* (2006.01)

(52) U.S. Cl.
USPC ........................................................ 530/412

(58) Field of Classification Search
None
See application file for complete search history.

(56) References Cited

U.S. PATENT DOCUMENTS

| 4,971,670 | A | 11/1990 | Faupel et al. |
| 5,972,613 | A | 10/1999 | Somack et al. |
| 6,096,872 | A | 8/2000 | Van Holten et al. |
| 6,190,608 | B1 | 2/2001 | Laub et al. |
| 2003/0166869 | A1 | 9/2003 | Vedantham et al. |
| 2004/0138424 | A1 | 7/2004 | Takeda et al. |

FOREIGN PATENT DOCUMENTS

| EP | 0344796 | 12/1989 |
| EP | 0628639 | 4/1992 |
| EP | 0610729 | 1/1994 |
| EP | 0893450 | 1/1999 |
| EP | 0960936 | 12/1999 |
| EP | 0962467 | 12/1999 |
| EP | 1225180 | 7/2002 |
| EP | 1247818 | 10/2002 |
| EP | 0313343 B2 | 7/2003 |
| JP | 5-504579 | 7/1993 |
| JP | 2000-319294 | 11/2000 |
| JP | 2000-351799 | 12/2000 |
| WO | 9207084 | 4/1992 |
| WO | 9420525 | 9/1994 |
| WO | 9522389 | 8/1995 |
| WO | 9635710 | 11/1996 |
| WO | 9703706 | 2/1997 |
| WO | 9919343 | 4/1999 |

OTHER PUBLICATIONS

Kipriyanov et al., "Generation of recombinant antibodies", Molecular Biotechnology, 1999, vol. 12, No. 2, pp. 173-201.
Harlow et al., "Antibody purification on protein-A columns", In: Antibodies, A laboratory manual, p. 310, 1988.
Fahrner et al, "Performance comparison of protein A affinity-chromatography sorbents for purifying recombinant monoclonal antibodies", Biotechnology and Applied Biochemistry, 1999, vol. 30, pp. 121-128.
Irvine Scientific (Santa Ana, CA) personal communication, Feb. 10, 2009, regarding HB-Pro medium.
Trizma hydrochloride, cat#T6666, product information sheet, Sigma, Inc (2009).
Sigma Buffer Chart, Sigma, Inc. (2000).
Oxenburgh et al, Use of streptomycin in the separation of nucleic acids from protein in a bacterial extract.) Nature. Sep. 25, 1965;207(5004):1416-7.
Aranha-Creado et al "Clearance of Murine Leukaemia Virus from Monoclonal Antibody Solutions by a Hydrophilic PVDF Microporous Membrane Filter," Biologicals 26: 167-172 (1998).
Bos et al: "Virus Validation of pH 4-Treated Human Immunoglobulin Products Produced by the Cohn Fractionation Process," Biologicals, vol. 26, No. 4, pp. 267-276, Dec. 1998.
F. Chiodi et al., "Isoelectric focusing of monoclonal immunoglobulin G, A and M followed by detection with the avidin-biotin system", Electrophoresis 1985, 6, 124-128.
EPO Communication—Third Party Observation Pursuant to Art. 115EPC mailed May 29, 2008.
International Preliminary Report on Patentability issued in PCT/JP2003/011642, Jun. 10, 2004
Lydersen et al: "Acid Precipitation of Mammalian Cell Fermentation Broth", Annals of the New York Academy of Sciences, New York Academy of Sciences, New York, NY, US, vol. 745, pp. 222-231 (Nov. 30, 1994).
Search Report dated Nov. 17, 2010, issued in a corresponding Application No. EP 10180577.8.

*Primary Examiner* — Sheridan Swope
(74) *Attorney, Agent, or Firm* — Browdy and Neimark, PLLC

(57) ABSTRACT

A method for manufacturing an antibody formulation in which DNA contaminants are removed by binding the antibody to a protein-A or probtin-G affinity column and eluting the antibody with an acidic eluting solution, preferably of low conductivity.

6 Claims, No Drawings

PROTEIN PURIFICATION METHOD

This application is a division of U.S. Ser. No. 10/527,455, filed Oct. 24, 2005, now U.S. Pat. No. 8,420,789, which is a 371 of PCT/JP03/011642, filed Sep. 11, 2003, which claims priority from Japanese application 265609/2002, filed Sep. 11, 2002.

TECHNICAL FIELD

The present invention relates to a method for purifying proteins, more specifically to a method for removing impurities such as DNA contaminants from a sample containing a physiologically active protein such as antibody molecules.

BACKGROUND ART

Advances in gene recombinant technology have enabled a stable supply of various protein formulations. In particular, a variety of recombinant antibody drugs, which are more selective than normal drugs, have been developed and entered clinical trial in recent years.

In these recombinantly-produced physiologically active protein-containing formulations, there is a need to remove host DNA and impurities (e.g., DNA contaminants) associated with viral contamination. Under present World Health Organization (WHO) criteria, the amount of DNA in biological drugs should not exceed 100 pg DNA/dose. To meet this criteria, in general, an aqueous medium containing host cell-derived physiologically active proteins is treated by anion-exchange chromatography, hydroxyapatite chromatography or a combination thereof, for the purpose of removing DNA.

In particular, in a case where a physiologically active protein is an antibody produced, recombinantly in mammalian host cells, the aqueous medium is treated by affinity column chromatography on Protein A or G before being purified by various types of chromatography, based on the binding property of Protein A or Protein G to IgG Fc chain.

By way of example, in JP KOHYO 5-504579, an antibody-containing aqueous medium obtained from mammalian cell culture is subjected to Protein A/G column chromatography to adsorb antibody molecules onto the column, followed by elution with an acidic solution (about 0.1 M citric acid, pH 3.0-3.5) to release the antibody molecules. The resulting acidic eluate is subjected sequentially to ion-exchange column chromatography and size exclusion column chromatography to give the purified antibody molecules.

However, these individual chromatographic processes and combinations thereof are time-, labor- and cost-consuming, as well as being complicated. Moreover, they fail to provide stable results.

Thus, the object of the present invention is to provide a simpler and less expensive method for purifying physiologically active proteins, especially antibodies, which can ensure removal of impurities such as DNA contaminants and viruses, and which can minimize a loss of physiologically active proteins.

DISCLOSURE OF THE INVENTION

As a result of extensive and intensive efforts made to overcome these problems, the inventors of the present invention have made the surprising finding that impurities such as DNA contaminants and viruses can be efficiently removed from, a physiologically active protein-containing sample without using complicated chromatographic processes when the sample is formed into an aqueous solution of low-conductivity at a pH below the isoelectric point of the physiologically active protein and then filtrated through a filter to remove the resulting particles. This finding led to the completion of the present invention.

Namely, the present invention provides the following.

(1) A method for removing impurities in a physiologically active protein-containing sample, which comprises the steps of:
 1) forming the physiologically active protein-containing sample into an aqueous solution of low conductivity having a pH equal to or lower than the isoelectric point of the physiologically active protein; and
 2) removing the resulting particles.

(2) The method according to (1) above, wherein the aqueous solution of low conductivity has a conductivity of 0 to 100 mM, as expressed in molarity.

(3) The method according to (1) or (2) above, wherein the aqueous solution of low conductivity has an ionic strength of 0 to 0.2.

(4) The method according to any one of (1) to (3) above, wherein the aqueous solution of low conductivity has a conductivity of 0 to 300 mS/m.

(5) The method according to any one of (1) to (4) above, wherein the solution is selected from aqueous solutions of hydrochloric acid, citric acid and acetic acid.

(6) The method according to any one of (1) to (5) above, wherein the pH of the aqueous solution is equal to or lower than the isoelectric point of the physiologically active protein and equal to or higher than pH 2.0.

(7) The method according to any one of (1) to (6) above, wherein the impurities are DNA contaminants.

(8) The method according to any one of (1) to (6) above, wherein the impurities are viruses.

(9) The method according to (7) above, wherein the physiologically active protein-containing sample has the DNA contaminants at a DNA concentration of 22.5 pg/ml or less after the treatment of removal of DNA contaminants.

(10) The method according to any one of (1) to (9) above, wherein the physiologically active protein is an antibody.

(11) The method according to (10) above, wherein the antibody is an IgG antibody.

(12) The method according to (10) or (11) above, wherein the antibody is a humanized monoclonal antibody.

(13) The method according to (12) above, wherein the antibody is a humanized anti-IL-6 receptor antibody.

(14) The method according to (12) above, wherein the antibody is a humanized anti-HM1.24 antigen monoclonal antibody.

(15) The method according to (12) above, wherein the antibody is a humanized anti-parathyroid hormone-related peptide antibody (anti-PTHrP antibody).

(16) The method according to any one of (1) to (9) above, wherein the physiologically active protein is granulocyte colony-stimulating factor.

(17) The method according to any one of (1) to (16) above, wherein the particles are removed by filtration through a filter.

(18) The method according to (1) above, wherein step 1) is accomplished by forming the physiologically active protein-containing sample into an acidic or alkaline aqueous solution of low conductivity, and adjusting the resulting sample with a buffer to a pH equal to or lower than the isoelectric point of the physiologically active protein.

(19) The method according to (1) above,
 wherein the physiologically active protein is an antibody, and
 wherein step 1) is accomplished by subjecting the antibody-containing sample to affinity chromatography on Protein A or G, eluting the sample with an acidic aqueous solution of low conductivity, and adjusting the resulting eluate with a buffer to a pH equal to or lower than the isoelectric point of the antibody.

(20) The method according to (18) or (19) above, wherein the buffer is an aqueous solution of Tris.

(21) A purified physiologically active protein obtainable by the method according to any one of (1) to (20) above.

(22) A method for manufacturing a medical protein formulation, which comprises a purification step in which the method according to any one of (1) to (20) above is used.

BEST MODE FOR CARRYING OUT THE INVENTION

Examples of a physiologically active protein contained in a sample to be purified by the method of the present invention include, but are not limited to, hematopoietic factors such as granulocyte colony-stimulating factor (G-CSF), granulocyte-macrophage colony-stimulating factor (GM-CSF), erythropoietin (EPO) and thrombopoietin, cytokines such as interferons, IL-1 and IL-6, monoclonal antibodies, tissue plasminogen activator (TPA), urokinase, serum albumin, blood, coagulation factor VIII, leptin, insulin, and stem cell growth factor (SCF). Among these proteins, preferred are G-CSF and antibodies including monoclonal antibodies, and more preferred are monoclonal antibodies. In an embodiment of the present invention using Protein A/G affinity chromatography, monoclonal antibodies are preferred for purification. Antibodies are categorized into IgG, IgA, IgE, IgD and IgM classes, with IgG antibodies being preferred.

The term "physiologically active protein" is intended to mean a protein having substantially the same biological activities as a corresponding physiologically active protein of mammalian (especially human) origin. Such a protein may either be native or genetically recombinant, preferably genetically recombinant. Genetically recombinant physiologically active proteins may be prepared by production in bacterial cells such as E. coli; yeast cells; or animal-derived cultured cells such as Chinese hamster ovary (CHO) cells, C127 cells or COS cells. The proteins thus prepared are isolated and purified in various manners before use. Such genetically recombinant, proteins encompass those having the same amino acid sequence as the corresponding native protein, as well as those comprising deletion, substitution or addition of one or more amino acids in the amino acid sequence, but retaining the biological activities mentioned above. Further, such proteins include those chemically modified with PEG, etc.

When a physiologically active protein is a glycoprotein, it may nave sugar chains of any origin, preferably of mammalian origin. Mammalian origins include, for example, Chinese hamster ovary (CHO) cells, BHK cells, COS cells and human-derived cells, with CHO cells being most preferred.

When a physiologically active protein is EPO, it may be prepared in any manner, for example, by obtaining from human urine in various manners or by producing with genetic engineering techniques in bacterial cells such as E. coli, yeast, cells, Chinese hamster ovary (CHO) cells, BHK cells, COS cells, human-derived cells or the like (e.g., as described in JP KOKAI 61-12288). EPO thus prepared is extracted, isolated, and purified in various manners before use. In addition, EPO may be chemically modified with PEG, etc. (see International Publication No. WO90/12874). EPO as used herein further includes those originally unglycosylated but chemically modified with PEG, etc. Likewise, EPO analogs are also included, which are modified to nave at least one additional site for N-linked or O-linked glycosylation in the amino acid sequence of EPO (see, e.g., JP KOKAI 08-151398, JP KOHYO 08-506023). Instead of increasing the number of glycosylation sites, EPO analogs may also be modified to have an increased content of sugar chains such as sialic acid for an increased amount of sugar chains.

When a physiologically active protein is G-CSF, any G-CSF can be used as long as it is highly purified. G-CSF as used herein may be prepared in any manner, for example, by obtaining from cultured human tumor cell lines or by producing with genetic engineering techniques in bacterial cells such as E. coli; yeast cells; or animal-derived cultured cells such as Chinese hamster ovary (CHO) cells, C127 cells or COS cells. G-CSF thus prepared is extracted, isolated, and purified in various manners before use. Preferred are those produced recombinantly in E. coli cells, yeast cells or CHO cells. The most preferred are those produced recombinantly in CHO cells. In addition, G-CSF may be chemically modified with PEG, etc. (see International Publication No. WO90/12874).

When a physiologically active protein is a monoclonal antibody, it may be prepared in any manner. In principle, a monoclonal antibody can be produced using known techniques by immunizing a sensitizing antigen in accordance with conventional procedures for immunization, fusing the resulting immunocytes with known parent cells through conventional procedures for cell fusion, and then screening monoclonal antibody-producing cells through conventional procedures for screening.

Alternatively, antibody genes are cloned, from hybridomas, integrated into appropriate vectors, and then transformed into hosts to produce antibody molecules using gene recombination technology. The genetically recombinant antibodies thus produced may also be used in the present invention (see, e.g., Carl, A. K. Borrebaeck, James, W. Larrick, THERAPEUTIC MONOCLONAL ANTIBODIES, Published in the United Kingdom by MACMILLAN PUBLISHERS LTD, 1990). More specifically, cDNA of antibody variable domains (V domains) is synthesized from, hybridoma mRNA using reverse transcriptase. Upon obtaining DNA encoding the target antibody V domains, the DNA is ligated to DNA encoding desired antibody constant domains (C domains) and integrated into an expression vector. Alternatively, the DNA encoding the antibody V domains may be integrated into an expression vector carrying the DNA of the antibody C domains. The DNA construct is integrated into an expression vector such that it is expressed under control of an expression regulatory region, e.g., an enhancer or a promoter. Host, cells are then transformed with this expression vector for antibody expression.

In the present invention, it is possible to use genetically recombinant antibodies (e.g., chimeric antibodies, humanized antibodies) that are artificially modified with a view to attenuating the characteristics as heteroantigen to human. These modified antibodies may be prepared in a known manner. A chimeric antibody is composed of variable domains of heavy and light chains from a non-human mammalian (e.g., mouse) antibody and constant domains of heavy and light chains from a human antibody. To obtain chimeric antibodies, DNAs encoding such mouse antibody variable domains may be ligated to DNAs encoding the human antibody constant domains, and then integrated into an expression vector, followed by transformation into a host for antibody production.

Humanized antibodies are also called reshaped human antibodies and are obtained by grafting complementarily determining regions (CDRs) of non-human mammalian (e.g., mouse) antibodies to replace those of human antibodies. Standard gene recombination procedures for this purpose are also known. More specifically, a DNA sequence designed to allow ligation between CDRs of mouse antibody and framework regions (FRs) of human antibody is synthesized by PCR from several oligonucleotides which are prepared to have sections overlapping with one another at the ends. The DNA thus obtained is ligated to DNA encoding human antibody constant domains, and integrated into an expression vector, followed by transformation into a host for antibody production (see European Patent Publication No. EP 239400 and International Publication No. WO 96/02576). The FRs of human antibody, which is ligated via CDRs, are selected such that the complementarity determining regions form a favorable antigen-binding site. If necessary, amino acid substitutions may be made in the framework regions of antibody variable domains such that the complementarity determining regions of reshaped humanized antibody may form an appropriate antigen-binding site (Sato, K. et al., Cancer Res. (1993) 53, 851-856).

A humanized anti-IL-6 receptor antibody (hPM-1) can be presented as a preferred example for such reshaped humanized antibodies (see International Publication No. WO92-19759). In addition to this, a humanized anti-HM1.24 antigen monoclonal antibody (see International Publication No. WO98-14580), a humanized anti-parathyroid hormone-related peptide antibody (anti-PTHrP antibody; see International Publication No. WO98-13388), a humanized anti-tissue factor antibody (see International Publication No. WO99-51743) and the like are also preferred for use in the present invention.

Procedures for obtaining human antibodies are also known. For example, human lymphocytes are sensitized in vitro with a desired antigen or a desired antigen-expressing cell, and the sensitized lymphocytes are then fused with human myeloma cells (e.g., U266) to give desired human antibodies having binding activity to the antigen (see JP KOKOKU 01-59878). Alternatively, transgenic animals having the entire repertories of human antibody genes may be immunized with an antigen to obtain desired human antibodies (see International Publication Nos. WO 93/12227, WO 92/03918, WO 94/02602, WO 94/25585, WO 96/34096 and WO 96/33735). There are additional techniques using human antibody libraries to give human antibodies by panning. For example, human antibody variable domains may each be expressed as a single-chain antibody (scFv) on the surface of phages by phage display technology, followed by selection of phages binding to the antigen. By analyzing genes of the selected phages, it is possible to determine DNA sequences encoding human antibody variable domains binding to the antigen. Once the DNA sequences of scFv binding to the antigen have been identified, the sequences may be used to construct appropriate expression vectors to obtain human antibodies. These techniques are already well known and can be found in WO 92/01047, WO 92/20791, WO 93/06213, WO 93/11236, WO 93/19172, WO 95/01438 and WO 95/15388.

Further, human antibodies produced in transgenic animals and the like are also preferred.

Furthermore, the antibody as used herein encompasses antibody fragments including Fab, (Fab')$_2$, Fc, Fc' and Fd, as well as reshaped antibodies including monovalent or polyvalent single chain antibodies (scFV).

As used herein, the term "physiologically active protein-containing sample" or an "antibody-containing sample" is preferably intended to mean a culture medium of mammalian cells (e.g., CHO cells) containing physiologically active protein molecules or antibody molecules produced by culture, which may further be subjected to partial purification or other certain treatment(s).

In a preferred embodiment of the present invention, impurities in a physiologically active protein-containing sample are removed by a method comprising the steps of:

1) forming the physiologically active protein-containing sample into an aqueous solution of low conductivity at a pH equal to or lower than the isoelectric point of the physiologically active protein; and 2) removing the resulting particles.

Any substance may be removed as an impurity by the method of the present, invention as long as it is not a target protein to be purified. Examples of such impurities include DNA contaminants, viruses, Protein A (eluted from columns), endotoxins, HCP (host cell-derived proteins), as well as medium components Hy-Fish (FL) and IGF, with DNA contaminants or viruses being preferred. As used herein, the term "DNA contaminants" is intended to mean DNA molecules present in a physiologically active protein-containing sample. Examples include host-derived DNAs and contamination-derived viral DNAs.

There is no particular limitation on the type of virus to be removed by the method of the present invention. Any virus, including DNA and RNA viruses, may be removed. Examples of RNA viruses include retroviruses (e.g., X-MuLV), reoviruses (e.g., Reo 3) and parvoviruses (e.g., MVM). Illustrative examples of viruses removed by the method of the present invention include, for example, X-MuLV, PRV, Reo 3, MVM, VSV, herpes simplex, CHV, Sindbis, mumps, vaccinia, Measle, Rubella, influenza, herpes zoster, cytomegalo, parainfluenza, EB, HIV, HA, HB, NANB, ATL, ECHO and parvovirus, with X-MuLV, Reo 3, MVM and PRV being preferred.

As used herein, the term "aqueous solution of low conductivity" is generally intended to mean an aqueous solution which has a molarity of 0 to 100 mM, preferably 0 to 50 mM, more preferably 0 to 30 mM, or which has an ionic strength of 0 to 0.2, preferably 0 to 0.12, or which has a conductivity of 0 to 300 mS/m, preferably 0 to 200 mS/m, more preferably 0 to 150 mS/m.

The isoelectric point of a physiologically active protein refers to the pH value at which the physiologically active protein has no apparent net charge in an aqueous solution. The isoelectric point can be determined in a manner known to those skilled in the art, for example, by means of isoelectric focusing in which a physiologically active protein is electrophoresed in solutions of various pH levels to determine the pH at which the protein will not migrate. A pH equal to or lower than the isoelectric point of a physiologically active protein is preferably a pH below the isoelectric point of the physiologically active protein.

When impurities are DNA molecules in the method of the present invention, the pH is preferably adjusted to a level equal to or lower than the isoelectric point of a physiologically active protein, so that the physiologically active protein is positively charged and the DNA molecules are negatively charged.

In general, DNA has very strong negative ion charges resulting from, phosphate groups in the backbone (phosphate groups found within strongly acidic phosphodiester bonds in nucleic acids have a pK value of about 1). For this reason, DNA can be negatively charged at any pH and it is possible to use a desired pH in the range of equal to or lower than the isoelectric point of a physiologically active protein. Since the pH level, required will vary among different types of physiologically active proteins, those skilled in the art may select a desired pH level in the range of equal to or lower than the isoelectric point of a physiologically active protein in a known manner, for example, by preparing multiple samples with different pHs and measuring their parameters such as % DNA removal and % protein recovery, as described in the Example section below. Such a pH is usually pH 2.0 or higher, preferably pH 3.0 or higher, and particularly preferably pH 4.0 or higher.

To confirm whether DNA molecules are negatively charged, known procedures may be used such as those using an electrophoretic titration curve (ETC) (see Ion Exchange Chromatography Principles and Methods, Pharmacia (latterly Amersham Biosciences), pp. 52-56).

Moreover, in the method of the present invention, a physiologically active protein-containing sample may also be formed into an acidic or alkaline aqueous solution of low conductivity, followed by adjusting the resulting sample with a buffer to a pH equal to or lower than the isoelectric point of the physiologically active protein.

Thus, in another preferred embodiment of the present invention, impurities in a physiologically active protein-containing sample are removed by a method comprising the steps of:

1) forming the physiologically active protein-containing sample into an acidic or alkaline aqueous solution of low conductivity;

2) adjusting the resulting sample with a buffer to a pH equal to or lower than the isoelectric point of the physiologically active protein; and 3) removing the resulting particles.

Impurities removed by the method of the present invention are as described above.

As used herein, the term "acidic aqueous solution of low conductivity" is intended to mean an aqueous solution of pH 2.0 to pH 3.9, preferably of pH 2.0 to pH 3.0, which has a molarity of 0 to 100 mM, preferably 0 to 50 mM, more preferably 0 to 30 mM, or which has an ionic strength of 0 to 0.2, preferably 0 to 0.12, or which has a conductivity of 0 to 300 mS/m, preferably 0 to 200 mS/m, more preferably 0 to 150 mS/m. The acidic aqueous solution may be selected from aqueous solutions of hydrochloric acid, citric acid, acetic acid and other acids. The type, conductivity and pH of acidic aqueous solution of low conductivity will vary depending on the type of physiologically active protein or antibody to be purified. Those skilled in the art will readily determine optimal conditions for these parameters in preliminary experiments as described herein.

Likewise, the term "alkaline aqueous solution of low conductivity" as used herein is intended to mean an aqueous solution usually of pH 7.5 to pH 13, which has a molarity of 0 to 100 mM, preferably 0 to 50 mM, more preferably 0 to 30 mM, or which has an ionic strength of 0 to 0.2, preferably 0 to 0.12, or which has a conductivity of 0 to 300 mS/m, preferably 0 to 200 mS/m, more preferably 0 to 150 mS/m. The pH of this solution will vary depending on the type of physiologically active protein or antibody to be purified.

In the method of the present invention, after a physiologically active protein-containing sample is formed into an acidic or alkaline aqueous solution of low conductivity, the resulting sample is adjusted with a buffer to a pH equal to or lower than the isoelectric point of the physiologically active protein. Examples of a buffer include Tris-HCl, phosphate, Tris, $N_2HPO_4$ and NaOH.

Moreover, in the present invention, in certain cases such as where a physiologically active protein is an antibody, an antibody-containing sample may usually be subjected to affinity chromatography on Protein A or G and eluted with an acidic aqueous solution of low conductivity, followed by adjusting the resulting eluate with a buffer to a desired pH in the range of equal to or lower than the isoelectric point of the physiologically active protein.

Thus, in yet another preferred embodiment, of the present invention, impurities in a physiologically active protein-containing sample are removed by a method comprising the steps of:

1) subjecting an antibody-containing sample to affinity chromatography on Protein A or G and eluting the sample with an acidic aqueous solution of low conductivity;

2) adjusting the resulting eluate with a buffer to a pH equal to or lower than the isoelectric point of the physiologically active protein; and 3) removing the resulting particles.

Impurities removed by the method of the present invention are as described above.

The acidic aqueous solution of low conductivity used in this method may be any of those listed above. Examples of a buffer include Tris-HCl, phosphate, Tris, $Na_2HPO_4$ and NaOH.

In the method of the present invention, the solution adjusted to a pH equal to or lower than the isoelectric point of the physiologically active protein in the above step, in turn, produces particles (i.e., becomes clouded). These particles may be removed by filtration through a filter to ensure efficient removal of impurities such as DNA contaminants. Examples of a filter available for filtration include, but are not limited to, a 1.0-0.2 μm Cellulose Acetate Filter System (Corning) or TFF.

Alternatively, these particles may also be removed by centrifugation or any other techniques for efficient particle removal; procedures for removal are not limited to filtration through a filter.

Without, being bound, by any particular theory, the inventors of the present invention estimate that when impurities are DNA molecules, each of these particles is a conjugate formed between physiologically active protein and DNA. They also estimate that when the pH is adjusted below the isoelectric point of a protein, the protein is positively charged and DNA molecules are negatively charged, resulting in conjugation between DNA and protein. Moreover, the conversion into an aqueous solution of low conductivity will further enhance conjugation. Particle removal by filtration results in a small loss of physiologically active protein because it is removed in the form of DNA-physiologically active protein conjugates. However, such a small loss constitutes only a few percent of the total amount of the physiologically active protein; about 90% of the physiologically active protein can be recovered, as will be described in the Example section below.

The inventors of the present invention also estimate that Protein A/G column chromatography alone may not be sufficient to ensure effective separation between DNA contaminant and physiologically active protein because DNA-protein conjugates are formed on the column resin. The physiologically active protein thus purified is available for use as a pharmaceutical formulation after further purification by cation-exchange chromatography, anion-exchange chromatography, hydroxyapatite chromatography, or combinations thereof.

Quantitative DNA assay may be accomplished by, but not limited to, Threshold Total DNA assay along with DNA extraction prior to the assay.

Quantitative virus assay may be accomplished by, but not limited to, $TCID_{50}$ (tissue culture infective dose (50%)) assay which is measured by viral infectivity in detection cells, in combination with RT/Q-PCR and Q-PCR which allow determination of the virus amount in fractions.

The present invention will now be further described in the following examples, which are not intended to limit the scope of the invention. Based on the detailed description, various changes and modifications will be apparent to those skilled in the art, and such changes and modifications fall within the scope of the invention.

EXAMPLES

Example 1

Investigation of Buffer Composition for Protein A Affinity Chromatography in Purifying hPM-1 (Humanized anti-IL-6 Receptor Antibody)

1.1. Test Procedures
(1) Test material (antibody-containing sample)

A sample containing the culture medium (hereinafter abbreviated as CM) of CHO cells producing hPM-1 antibody (humanized anti-IL-6 receptor antibody), which had been centrifuged to remove the cells and stored at −80° C., was filtered through a 0.22 μm Cellulose Acetate (abbreviated as CA) Filter System (CORNING) and used as a test sample for purification investigation. The hPM-1 antibody was prepared as described in Reference Example 2 of JP KOKAI 08-99902 using the human elongation factor Iα promoter shown in Example 10 of International Publication No. WO92/19759 (isoelectric point: pH 9.0).
(2) Instrument Used for Examination
For HCl Eluate
HPLC: L-6200 Intelligent Pump (HITACHI)
    L-4200 UV-VIS Detector (HITACHI)
    D-2500 Chromato-Integrator (HITACHI)
Column: HR5/2 (Pharmacia), 5 mm I.D.×20 mm H
Media: POROS 50A (PerSeptive), 0.4 ml
    Lot; A250-039, Code; SPECIAL
For Particles
HPLC: Waters PrepLC4000 System (Waters)
    Waters2000 System. Controller (Waters)
    Waters486 Tunable Absorbance Detector (Waters)
    Waters741 Data Module (Waters)
Spectrophotometer: U-2000 (HITACHI)
Column: XK26 (Pharmacia), 26 mm I.D.×100 mm H
Media: POROS 50A (PerSeptive), 53 ml
    Lot; A250-039, Code; SPECIAL
(3) Analysis and Assay
hPM-1 assay:
    hPM-1 is assayed by reversed-phase HPLC on a PLRP-S column (Polymer Laboratories) with a linear gradient.
DNA Assay:
    DNA is measured by Threshold Total DNA assay. Prior to the assay, DNA extraction is performed (e.g., using a DNA extracter kit, Wako Pure Chemicals Industries, Ltd.). Likewise, a Threshold Total DNA assay kit (Molecular Devices) is used for the measurement.
Turbidimetry:
    Each test sample is monitored for particle formation by measuring its absorbance at 660 nm in a spectrophotometer U-2000 (HITACHI).
1.2. Investigation of Elution Conditions Elution conditions were investigated at various buffer compositions for elution in Protein A affinity chromatography by measuring % recovery of hPM-1 and DNA removal by elution. The above antibody-containing sample was subjected to the column under the conditions indicated in Table 1 below. Protein A resin was equilibrated with the equilibration buffer indicated in Table 1 and then loaded with the above antibody-containing sample, followed by Washing 1, Washing 2 and elution. The elution profile was monitored at A280 nm to isolate a protein peak. In the table, C-P Buffer denotes citrate-phosphate buffer.

TABLE 1

| | Elution method 1 | Elution method 2 | Elution method 3 |
|---|---|---|---|
| Equilibration | 1M NaCl/100 mM C-P Buffer pH 7.5 | 1M NaCl/10 mM C-P Buffer pH 7.5 | 1M NaCl/100 mM C-P Buffer pH 7.5 |
| Washing 1 | 1M NaCl/100 mM C-P Buffer pH 7.5 | 1M NaCl/10 mM C-P Buffer pH 7.5 | 1M NaCl/100 mM C-P Buffer pH 7.5 |
| Washing 2 | 100 mM C-P Buffer pH 7.5 | 10 mM C-P Buffer pH 7.5 | 100 mM C-P Buffer pH 7.5 |
| Elution | 100 mM C-P Buffer pH 2.6 | 2.5 mM HCl pH 2.6 | 2.5 mM HCl pH 2.6 |

No chromatographic difference was observed among Elution methods 1, 2 and 3.

Each Elution fraction was adjusted to pH 7.0 with a 300 mM. Tris solution, indicating that particles were generated in the fractions eluted with HCl (Elution methods 2 and 3). Further investigation was performed to determine the correlation between particle formation and % recovery of hPM-1 or the amount of residual DNA.

To examine the particle correlation, the HCl eluate from Elution method 2 was supplemented, with NaCl and analyzed for the correlation between NaCl concentrations (0 mM, 50 mM, 100 mM) and various factors. In the analysis of the correlation between NaCl concentrations and various factors, filtered, and unfiltered samples were prepared as follows: each Protein A Elution fraction supplemented with NaCl was adjusted to pH 7.0 with a 300 mM Tris solution and then filtered or unfiltered through a 0.22 μm CA Filter. The filtered and unfiltered samples were measured for % recovery of hPM-1 (filtered samples only) and the amount of residual DNA.

1.3. % Recovery

The % recovery of hPM-1 was measured for the individual elution methods. As a result, the % recovery was as high as 98.6% in Elution method 1. In contrast, the % recovery ranged from 83.8% to 97.1% in Elution method 2 and from 83.5% to 93.7% in Elution method 3; these variations were estimated to be due to the smallness of examination scale (resin volume: 0.4 ml). When the purification scale was increased, it was confirmed that the % recovery of hPM-1 was stabilized at 90% or more (Elution method 2). Thus, the % recovery of hPM-1 was also found to remain high even in HCl elution.

1.4. Correlation Between NaCl Concentrations in the HCl Eluate and Various Factors Table 2 summarizes the analysis of the correlation between NaCl concentrations in the HCl eluate and various factors.

TABLE 2

| NaCl concentration | 0 mM | 50 mM | 100 mM |
|---|---|---|---|
| Turbidity (pH unadjusted) | 0.004 | 0.007 | 0.011 |
| Turbidity (pH adjusted) | 0.252 | 0.049 | 0.020 |
| % Recovery of hPM-1 (filtered) (%) | 81 | 86 | 88 |
| Amount of DMA (unfiltered) (pg DNA/mg hPM-1) | 98 | 220 | 241 |
| Amount of DNA (filtered) (pg DNA/mg hPM-1) | 11 | 30 | 250 |

For the filtered samples, the % recovery of hPM-1 was 88% at 100 mM NaCl, 86% at 50 mM NaCl and 81% at 0 mM NaCl. The amount of residual DNA was low at 0 mM NaCl in both filtered and unfiltered samples. In particular, the filtered sample supplemented with 0 mM NaCl had a very low DNA content of 11 pg DNA/mg hPM-1.

The pH-adjusted, samples with a higher turbidity tend to provide a lower % recovery of hPM-1 and a smaller amount of residual DNA after filtration. This result suggests a high possibility that hPM-1 and DNA both contribute to particle formation. It is estimated that hPM-1 and DNA probably interact with each other to form particles by adjusting the pH to 7.0. In view of achieving a higher % recovery of hPM-1, it is preferable to increase the NaCl concentration in the HCl eluate. In view of decreasing an amount of residual DNA, on the other hand, it is desirable to eliminate NaCl supplementation into the HCl eluate.

Example 2

Purification of Humanized Anti-PTHrP Antibody

A sample containing a humanized anti-PTHrP antibody (a culture medium from CHO cell culture, filtered through 0.45 and 0.2 μm CA SARTOBRAN P filters (sartorius)) was purified by Protein A affinity column chromatography under the conditions indicated below. The anti-PTHrP antibody was prepared as described in International Publication No. WO98/13388 (isoelectric point: pH 8.3).
2.1. Experimental Conditions
Purification apparatus: AKTA explorer (Amersham Pharmacia Biotech)
Column: HR5/5, C10, XK-26 (Amersham Pharmacia Biotech)
Resin: rProtein A Sepharose Fast Flow
Load: direct load of the culture medium (pH 6.6 to pH 7.5)
Adjustment of elution fraction: elution fractions are adjusted to various pH levels with a 1 M aqueous Tris solution and then filtered through a 0.2 μm Cellulose Acetate (hereinafter abbreviated as CA) to remove DNA (the conditions are examined in (1) below).

The Protein A column was sufficiently equilibrated with 150 mM NaCl-containing citrate-phosphate buffer (pH 7.5) and then loaded with the above antibody-containing CM. Subsequently, the column was washed with 150 mM NaCl-containing citrate-phosphate buffer (pH 7.5) to remove unbound impurities, further washed with citrate-phosphate buffer (pH 7.5) to decrease the conductivity, and then eluted with 20 mM aqueous citric acid. The elution profile was monitored at A280 nm to isolate a protein peak. This Protein A elution fraction was used for the following examination of conditions.
2.2. Examination of Removal Conditions for Residual DNA in the Eluate To ensure efficient removal of residual DNA, the optimal pH for filtration through a filter was investigated. The Protein A elution fraction was adjusted with a 1.0 M aqueous Tris solution to the following pH levels: 2.7 (unadjusted), 4.0, 4.5, 5.0, 5.5, 6.0, 6.5, 7.0 and 7.5. Subsequently, each sample was allowed to stand for a given period of time, filtered through a 0.22 μm CA filter, and then adjusted to pH 7 with a 1.0 M aqueous Tris solution, followed by DNA assay. Table 3 lists the examined pH levels and standing periods, along with the amount of residual DNA.

As shown in the table, the amount of residual DNA was below the detection limit at pH 5.5 and pH 6.0 in all cases where the samples were allowed to stand for 0, 6 and 24 hours. Also, the removal of residual DNA reached a peak around pH 5.5 and pH 6.0, whereas decreased efficiency of DNA removal was observed at higher and lower pH levels.

Example 3

Purification of Humanized Anti-HM1.24 Antigen Monoclonal Antibody

A sample containing a humanized anti-HM1.24 antigen monoclonal antibody (a culture medium from CHO cell culture) was purified by Protein A affinity column chromatography under the conditions indicated in Table 4 below. The anti-HM1.24 antigen monoclonal antibody was prepared as described in International Publication No. WO98/14580 (isoelectric point: pH 9.0).
3.1. Experimental Conditions
Column: rProtein A FF, 5 mL (16 mm ID×25 mm H)
Flow rate: 5 mL/min (150 cm/h)
Sample: direct load of the culture medium

TABLE 4

| Equilibration (20 CV) | 10 mM C-P Buffer, 1M NaCl, pH 7.5 |
| Load | Direct load of CM |
| Washing 1 (20 CV) | 10 mM C-P Buffer, 1M NaCl, pH 7.5 |
| Washing 2 (20 CV) | 10 mM C-P Buffer, pH 7.5 |
| Elution (10 CV) | Citric acid, pH 2.5 |
| Washing 3 (4 CV) | 0.1M NaOH |

The Protein A column was sufficiently equilibrated with 150 mM NaCl-containing citrate-phosphate buffer (pH 7.5) and then loaded with the above antibody-containing CM. Subsequently, the column was washed with 150 mM NaCl-containing citrate-phosphate buffer (pH 7.5) to remove unbound impurities, further washed with citrate-phosphate buffer (pH 7.5) to decrease the conductivity, and then eluted with 20 mM aqueous citric acid. The elution profile was monitored at A280 nm to isolate a protein peak. This Protein A elution fraction was used for the following investigation of conditions.
3.2. Investigation of Removal Conditions for Residual DNA in the Eluate To ensure efficient removal of residual DNA, the optimal pH for filtration through a filter was investigated. The Protein A elution fraction was adjusted with a 1.0 M aqueous Tris solution to the following pH levels (pH=4.5-7.5). Subsequently, each sample was allowed to stand for a given period of time, filtered through a 0.22 μm CA filter, and then adjusted to pH 7 with a 1.0 M aqueous Tris solution, followed by DNA assay and reversed-phase HPLC for assay of the humanized anti-HM1.24 antigen monoclonal antibody. Table 5 shows the

TABLE 3

Removal of residual DNA (unit: pg/mL)

| | pH 7.5 | pH 7.0 | pH 6.5 | pH 6.0 | pH 5.5 | pH 5.0 | pH 4.5 | pH 4.0 | Direct (pH 2.7) |
|---|---|---|---|---|---|---|---|---|---|
| 0 hr. | 984 | 83.3 | 53.8 | <22.5 | <15.0 | 7.2 | 54.1 | 32,052 | 40,878 |
| 6 hr. | 816 | 51.9 | <15.0 | <22.5 | <15.0 | <15.0 | 44.0 | 38,172 | 42,078 |
| 24 hr. | 310 | 46.6 | <15.0 | <22.5 | <15.0 | <15.0 | 39.7 | 42,528 | 30,222 |

(DNA in the culture medium: 6,637,200 pg/mL; DNA in the unfiltered sample: 25,110 pg/mL)

results of DNA assay, while Table 6 shows the yield of the humanized anti-HM1.24 antigen monoclonal antibody.

TABLE 5

Removal of residual DMA (unit: pg/ml)

Experiment 1

|  | pH 7.5 | pH 6.5 | pH 5.5 |
|---|---|---|---|
| 0 h | 1142 | 624 | 113 |
| 6 h | 3288 | 1157 | 117 |

(DNA in the culture medium: 235200 pg/ml)

Experiment 2

|  | pH 5.5 | pH 5.0 | pH 4.5 |
|---|---|---|---|
| 0 h | 137 | 67 | 86 |
| 6 h | 94 | 34 | 164 |

(DNA in the culture medium: 5448000 pg/ml; DNA in the unfiltered sample: 4330 pg/ml)

TABLE 6

% Recovery of humanized anti-HM1.24 antigen monoclonal antibody by filtration

|  | pH 5.5 | pH 5.0 | pH 4.5 |
|---|---|---|---|
| 0 h | 98.1% | 89.6% | 87.8% |
| 6 h | 89.3% | 91.1% | 98.6% |

Although, the samples purified by Protein A affinity chromatography were still rich in DNA, Experiment 1 indicated that the amount of DNA decreased with decrease in pH in the order of pH 7.5, pH 6.5 and pH 5.5, and that there was a tendency to remove more DNA at 0 hours than at 6 hours. In Experiment 2, the same experiment was carried out under conditions of pH=4.5, 5.0 and 5.5, indicating that DNA was sufficiently removed to the same extent, regardless of pH and standing period within the tested, range. In addition, the calculation of % recovery indicated little loss of the humanized anti-HM1.24 antigen monoclonal antibody.

Example 4

Purification of Granulocyte Colony-Stimulating Factor (G-CSF)

A G-CSF-containing sample (from CHO cell culture; Chugai Pharmaceutical Co., Ltd.) was used for the following examination of conditions (isoelectric point: pH 5.5-5.7).

4.1. Investigation of Removal Conditions for Residual DNA in the Eluate

To ensure efficient removal of residual DNA, the optimal pH for filtration through a filter was investigated. The G-CSF-containing sample was diluted in an acidic solution of low conductivity (2.5 mM aqueous HCl) and further formed into an acidic aqueous solution of low conductivity using 20% hydrochloric acid, followed by addition of sample DNA. The G-CSF-containing sample thus treated was adjusted with a 1.0 M aqueous Tris solution to the following pH level (pH=4.3 or 6.6) and then filtered through a 0.22 CA filter. Subsequently, DNA assay was performed on both filtered and unfiltered fractions. Table 7 shows the results of DNA assay.

TABLE 7

Removal of residual DNA (unit: pg/ml)

| pH for filtration | pH 6.6 | pH 4.3 |
|---|---|---|
| Unfiltered | $4.3 \times 10^5$ | $4.3 \times 10^5$ |
| Filtered | $2.8 \times 10^4$ | <90 |

This investigation confirms efficient reduction of DNA in the G-CSF-containing sample rich in DNA when the sample was filtered at pH 4.3; namely, the amount of residual DNA was below the assay limit of detection.

Example 5

Effects of Virus Removal on the Purification of hPM-1 (Humanized anti-IL-6 Receptor Antibody)

5.1 Test Material (Antibody-Containing Sample)

Samples containing the culture medium (CM) of CHO cells producing hPM-1 antibody (humanized IL-6 receptor antibody), which had been centrifuged to remove the cells and stored at −80° C., were supplemented with X-MuLV, Reo3 and MVM, respectively, followed by filtration through a 0.45 µm filter (Bottle Top Filter, CORNING) for use as test samples for purification investigation. The hPM-1 antibody was prepared as described in Example 1. The viruses used for examination were each obtained from ATCC (American Type Culture Collection).

5.2 Purification by rProtein Column Chromatography

The virus-supplemented samples prepared in 5.1 were purified by rProtein Column Chromatography. Detailed conditions are as shown below.

Resin: rProteinA Sepharose Fast Flow
Instrument: AKTA explorer100, AKTApurifier
Column: XK16/20, XK16/40
Resin height: 11.5 cm
Elution conditions
   Equilibration: 1 mol/L NaCl, 20 mmol/L C-P Buffer,
     pH 7.5±0.2, Conductivity 8.5±0.5 S/m
   Washing 1: 1 mol/L NaCl, 20 mmol/L C-P Buffer,
     pH 7.5±0.2, Conductivity 8.5±0.5 S/m
   Washing 2: 10 mmol/L C-P Buffer,
     pH 7.7±0.2, Conductivity 165±20 mS/m
   Elution: 2.5 mmol/L HCl,
     pH 2.7±0.2, Conductivity 107±10 mS/m 5.3 Low pH Treatment The elution fractions obtained in 5.2 were adjusted to pH 3.2±0.1 with 1 mol/L hydrochloric acid and held at a room temperature of 15±5° C. for 30 minutes or longer. Subsequently, each elution fraction was adjusted to pH 7.2±0.1 with a 300 mmol/L Tris solution, 40.0 mL of which was then filtered under a pressure of 0.03±0.01 MPa using a filtration unit equipped with a glass fiber filter (Millipore)(0.2 µm, PALL) connected to the primary side and a BioInert (0.2 µm, PALL) (a PALL filter holder equipped with a Φ15 mm adjuster) connected to the secondary side.

5.4 Detection of Viruses

All the samples collected were measured by $TCID_{50}$ assay. In the clearance capacity test for X-MuLV and MVM, these viruses were detected not only by $TCID_{50}$ assay which was measured by viral infectivity in detection cells, but also by RT/Q-PCR and Q-PCR which allowed determination of the virus amount in fractions.

5.5 Results

The results of detection in 5.4 are shown in the tables below.

TABLE 8

| | Virus liter (TCID$_{50}$ assay: Log$_{10}$/mL) | | | |
|---|---|---|---|---|
| | Reo3 | | MVM | |
| | Run 1 | Run 2 | Run 1 | Run 2 |
| Unfiltered | 5.76 | 5.76 | 4.80 | 4.18 |
| Filtered | ≤1.03 | ≤1.03 | ≤1.03 | ≤1.03 |

TABLE 9

| | Virus liter (PCR: Log$_{10}$ Copies/5 μL) | | | |
|---|---|---|---|---|
| | X-MuLV | | MVM | |
| | Run 1 | Run 2 | Run 1 | Run 2 |
| Unfiltered | 5.05 | 4.77 | 4.18 | 2.83 |
| Filtered | ≤1.90 | ≤1.90 | ≤1.30 | ≤1.90 |

As shown above, the purification process of the present invention achieves very high LRVs (Logarithmic Reduction Values) for all the tested viruses and this examination confirms that the viruses were removed to a level below the assay limit of detection after low pH treatment and filtration.

INDUSTRIAL APPLICABILITY

The method of the present invention enables efficient removal of impurities such as DNA contaminants and viruses in a very simple manner, and is significantly advantageous in purifying physiologically active proteins, especially antibodies. The method achieves an extremely low DNA concentration (e.g., 22.5 pg/ml) when impurities are DNA molecules, while it achieves an extremely low virus titer (e.g., 1.03 (expressed in Log$_{10}$/mL), as measured by TCID$_{50}$ assay) when impurities are viruses. The method of the present invention also enables cost reduction and has great significance in this field.

The invention claimed is:

1. A method for manufacturing a medical protein formulation, wherein the protein is an antibody,
   which comprises providing a composition comprising a medical protein and suspected of containing DNA contaminants, and removing such DNA contaminants by the steps comprising:
   1) applying the composition to a protein-A or protein-G affinity column, which binds the medical protein,
   2) washing the column to elute non-bound components of the composition,
   3) eluting the bound medical protein with an aqueous solution of pH of 2.0 to 3.9 and an ionic concentration of 50 mM or less, thereby forming an acidic aqueous solution of the medical protein having an ionic concentration of 50 mM or less and a pH of 2.0 to 3.9,
   4) forming particles containing the DNA contaminants by a step consisting of adjusting the pH of the eluate solution to a pH of from 4.0 to 7.5 by adding a buffer, and
   5) removing the particles of step 4),
   thereby obtaining the medical protein formulation.

2. The method according to claim 1, wherein the particle-containing solution of step 4) has a conductivity of 300 mS/m or less.

3. The method according to claim 1, wherein the aqueous solution for eluting the bound medical protein of step 3) is selected from the group consisting of aqueous solutions of hydrochloric acid, citric acid and acetic acid.

4. The method according to claim 1, wherein after the removal of DNA particles, the DNA contaminants are at a DNA concentration of 22.5 pg/ml or less.

5. The method according to claim 1, wherein the buffer is an aqueous solution of Tris.

6. The method according to claim 1 wherein the antibody is a genetically produced antibody or a modified antibody.

* * * * *